US00PP24951P3

(12) United States Plant Patent
Lewis

(10) Patent No.: US PP24,951 P3
(45) Date of Patent: Oct. 7, 2014

(54) **COLUMNAR *PARROTIA PERSICA* PLANT NAMED 'JL COLUMNAR'**

(50) Latin Name: *Parrotia persica*
Varietal Denomination: JL Columnar

(76) Inventor: John Lewis, Salem, OR (US)

( * ) Notice: Subject to any disclaimer, the term of this patent is extended or adjusted under 35 U.S.C. 154(b) by 262 days.

(21) Appl. No.: 13/200,724

(22) Filed: Sep. 28, 2011

(65) Prior Publication Data

US 2013/0081160 P1 Mar. 28, 2013

(51) Int. Cl.
*A01H 5/00* (2006.01)

(52) U.S. Cl.
CPC ..... *A01H 5/00* (2013.01)
USPC ..... Plt./216

(58) Field of Classification Search
USPC ..... Plt./216, 263.1
See application file for complete search history.

*Primary Examiner* — Kent L Bell
(74) *Attorney, Agent, or Firm* — Chernoff Vilhauer McClung & Stenzel LLP

(57) ABSTRACT

A new cultivar of Ornamental *Parrotia persica* plant named 'JL Columnar' that is characterized by a columnar growth habit, leaves which are solid purple when they break dormancy in the spring, turn to green with purple halo margins, and display a two phase fall color. The leaves are slightly smaller than in the genus.

7 Drawing Sheets

Genus: *Parrotia.*
Species: *persica.*
Varietal denomination: 'JL Columnar'.

BACKGROUND OF THE INVENTION

The new *Parrotia persica* tree was discovered as a seedling of unknown parentage while growing in a cultivated area tended by man.

Plants of the new variety have been asexually reproduced at Salem, Oreg., U.S.A., through the use of softwood cuttings. The characteristics of the new variety have been found to be strictly transmissible by such asexual propagation, and the new variety reliably reproduces in a true-to-type manner from one generation to another.

BRIEF SUMMARY OF THE INVENTION

The subject variety exhibits the following combination of characteristics:

(a) Displays a columnar habit
(b) Leafs break dormancy in the spring with solid purple leaves
(c) New leaves transform to green with purple halo margins
(d) Displays two phase fall color
(c) Forms slightly smaller leaves The variety can be readily distinguished from previously known *Parrotia persica* varieties in view of the recited combination of characteristics. The growth habit is columnar in form and differs significantly from the species which is rounded to broad-rounded by a horizontal branching appearance. The shape is similar to no other cultivars known to the Inventor. Additionally, it forms leaves which are slightly smaller than the genus in length and width.

The variety meets the needs of the horticultural industry and is well suited for growing as attractive distinctive ornamentation in the landscape.

BRIEF DESCRIPTION OF THE PHOTOGRAPHS

DETAILED BOTANICAL DESCRIPTION OF PREFERRED EMBODIMENT

The chart used in the identification of color is The R.H.S. Colour Chart of The Royal Horticultural Society, London, England. Other reference to color is to be accorded its ordinary dictionary significance. The description is based upon the observation of plants of the new variety having an age of approximately 4 years while being grown outdoors at Salem, Oreg., U.S.A.

Figure 1:
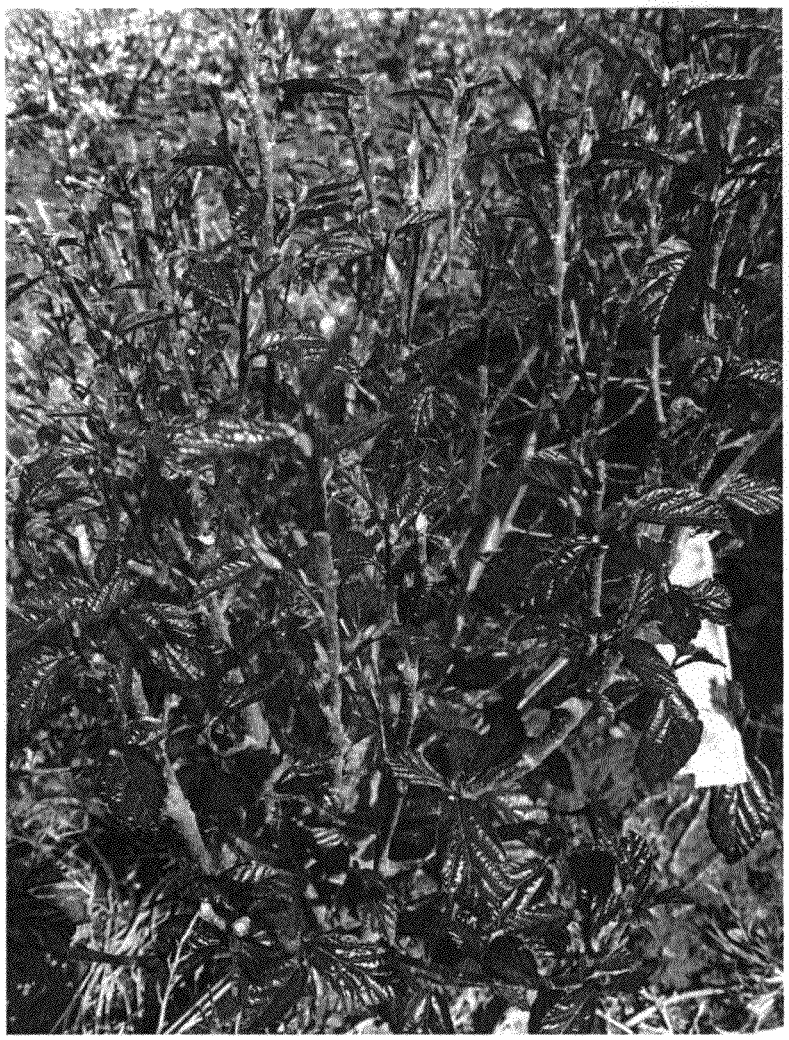
FIG. 1 illustrates a close-up view of a 4 year old specimen of the new variety, growing on its own root.
Figure 2:
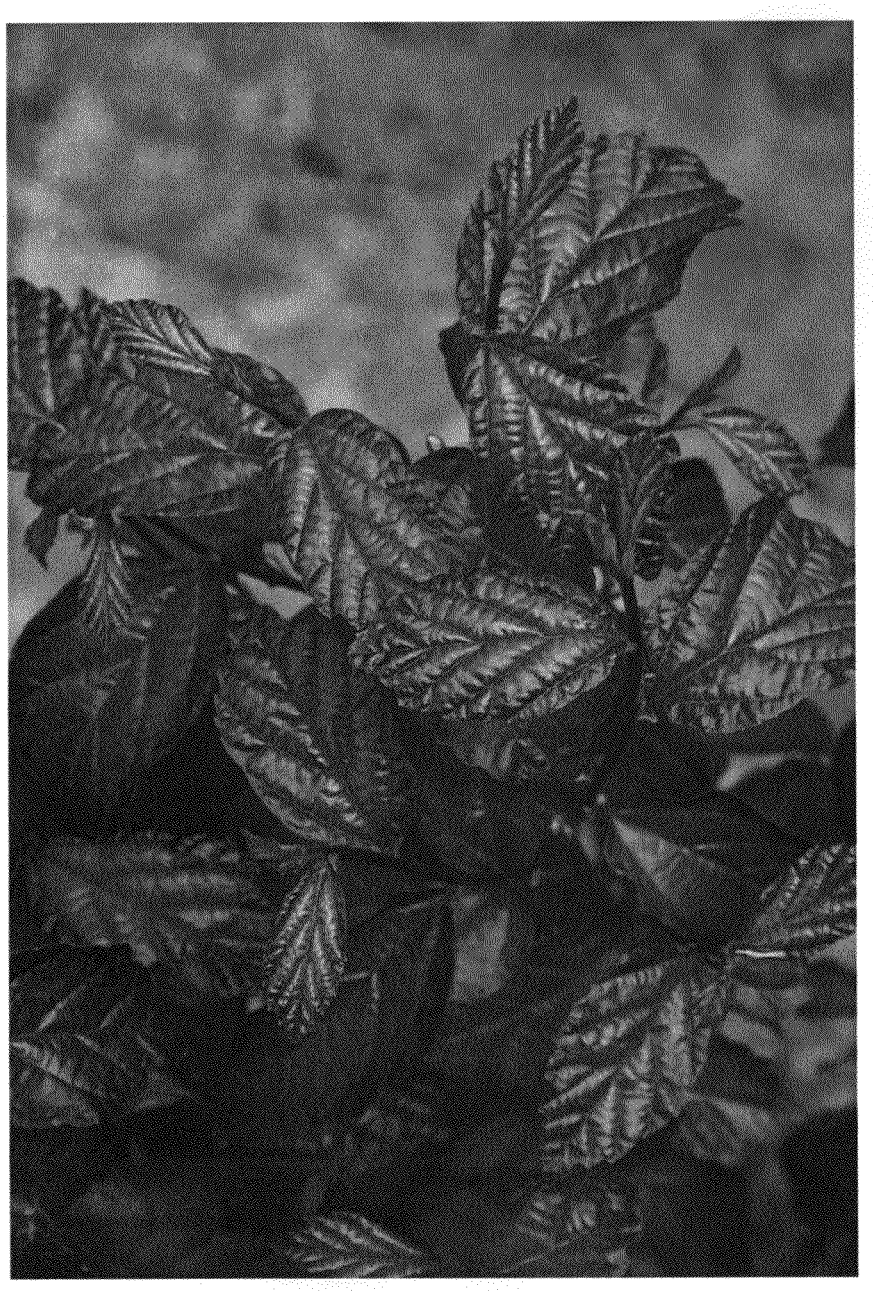
FIG. 2 illustrates the same 4 year old, own root specimen, up close to show the emerging purple leaves of the new variety.
Figure 3:
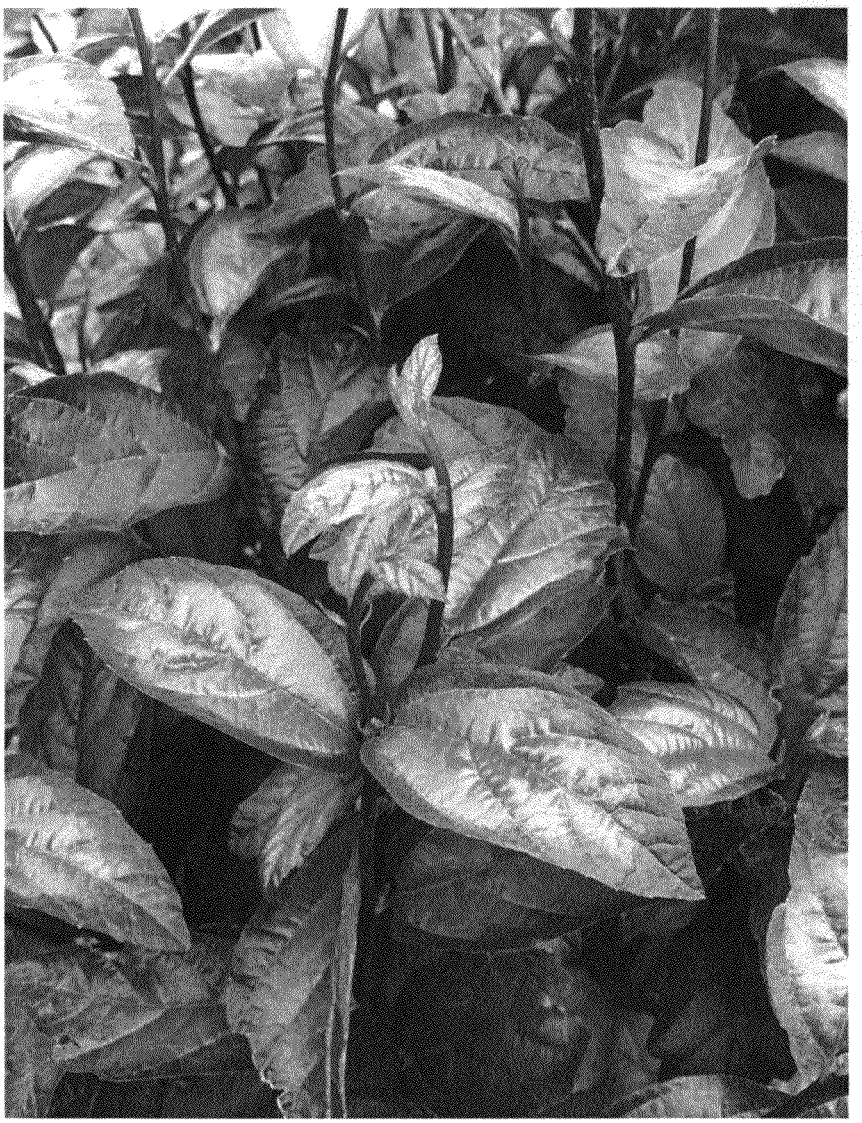
FIG. 3 illustrates the leaves transform to green with purple halo margins.
Figure 4:
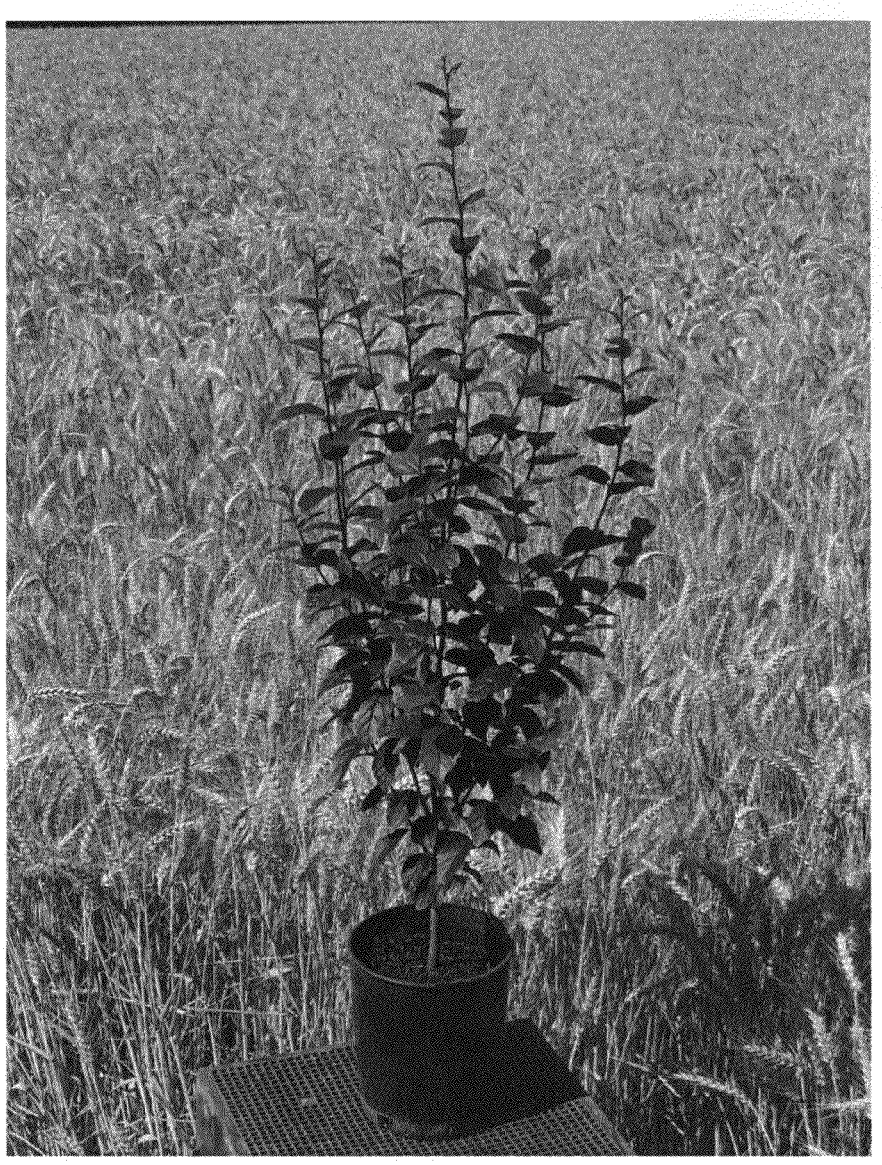
FIG. 4 illustrates the columnar growth habit of the new variety.
Figure 5:
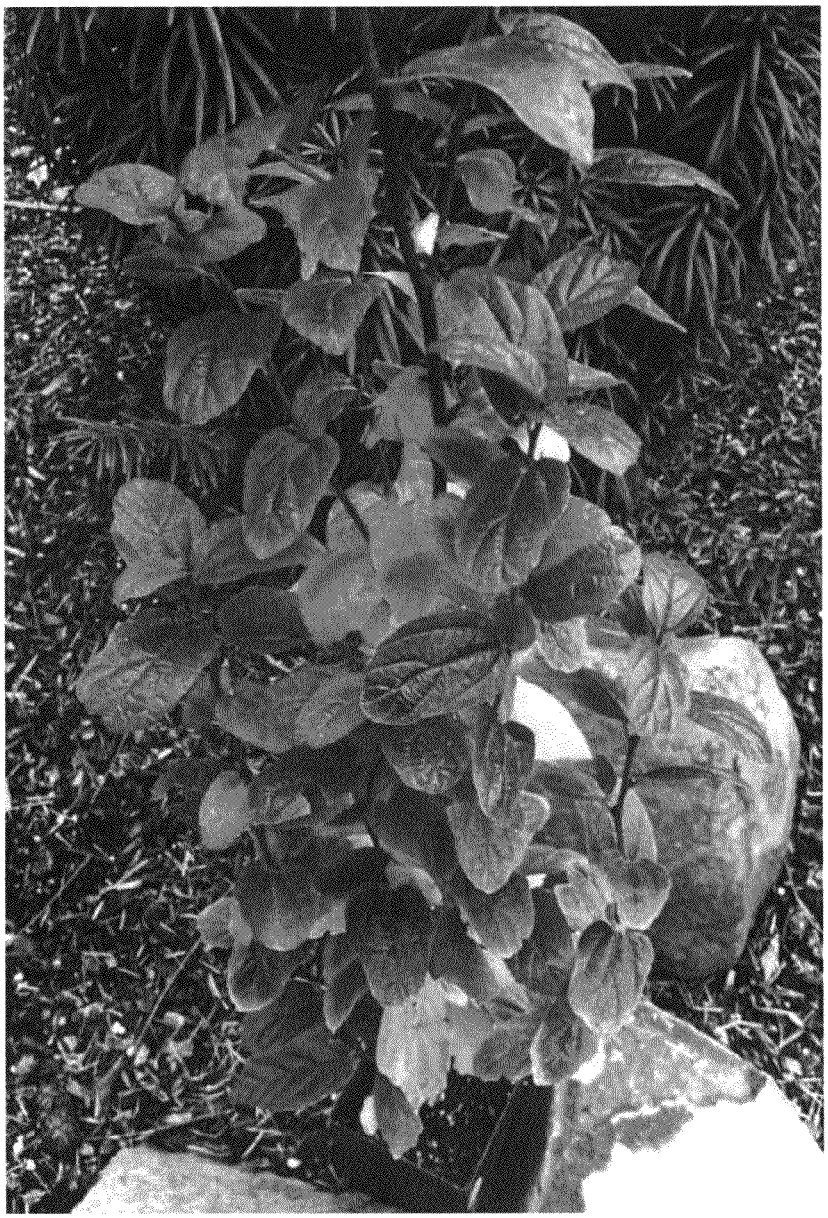
FIG. 5 illustrates the first phase of the fall color change.
Figure 6:
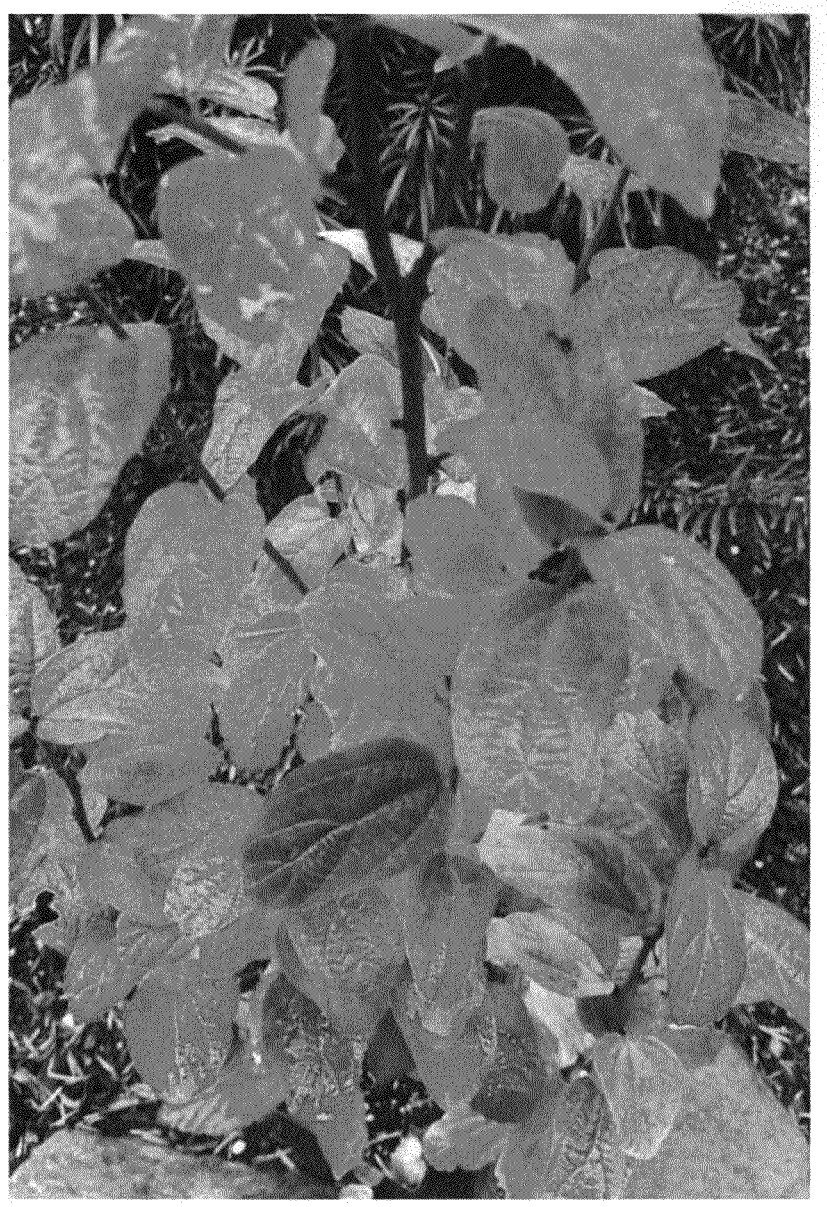
FIG. 6 illustrates the second phase of the fall color change.

The new variety exhibits an extremely columnar growth habit with a fast growth rate as shown in FIG. 4 in this regard.

Figure 7:
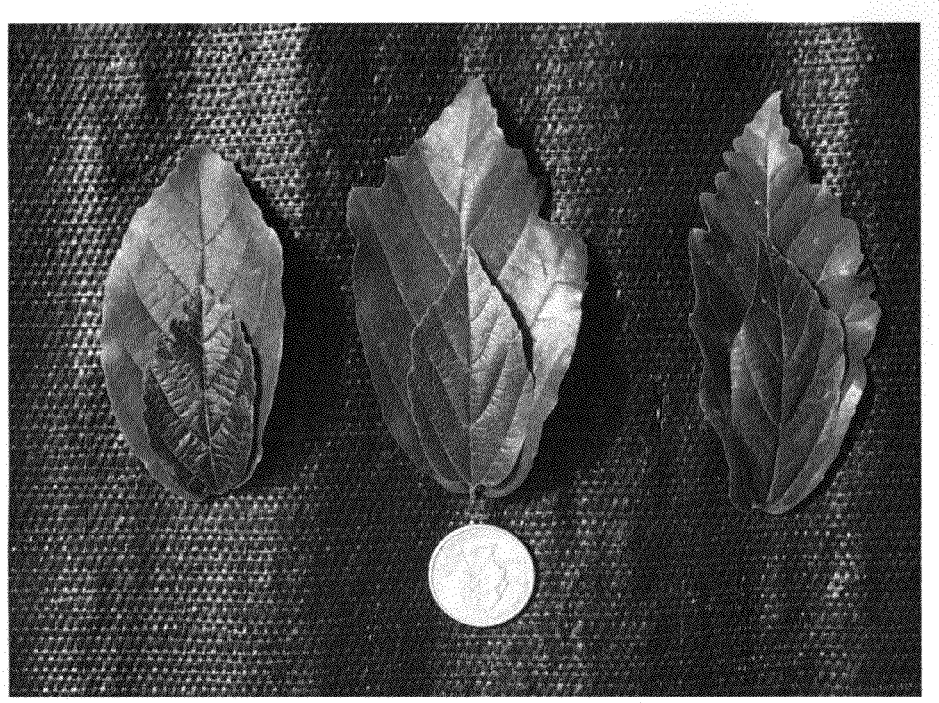
FIG. 7 illustrates the mature leaves of the new variety that are smaller than the species *Parrotia persica*, and also smaller than other cultivars known to the inventor.

The vegetative parts of the new variety are typical of the genus except as specifically indicated hereafter. The alternate, simple oval to obovate-oblong leaves are lanceolate caduceus stipules, obtuse, rounded to sub-cordate at base, coarsely crenate-dentate about the middle, glabrous above with sparse pubescence below, undulate, lustrous. See FIG. 7 in this regard. The leaf apex of *Parrotia persica* is acute. The leaf apex of the new variety is acute-acuminate. The petiole is approximately ⅛" in length and 3/32" in diameter which is typical of the species. The color of the petiole of the new variety is Red-Purple Group 59A, similar to *Parrotia persica*. The species leaves are normally 2½" to 5" long and 1" to 2½" wide. The new variety has leaves approximately 2½ to 3½" in length and around 1½" to 2" in width. Compared to plants of *Parrotia persica*, known to the Inventor, its leaves are much smaller, and narrower.

The emerging leaves of the new variety in the spring on the upper surface are like Red Purple Group 71A. As new spring growth emerges and leaves form to full size, leaves transition to a mixture of Greyed-Purple 187A, 187B, 187C and 187D. The observed emerging leaf under surface color is Green Group 141B, in comparison to typical *Parrotia persica*, which is Green Group 140B. As leaves mature, the upper, middle and lower surfaces deepen to Green Group 141A with a haloed margin of Red-Purple Group 74A. The upper, middle, and lower surfaces of mature leaves are solid Color Group 141A.

The twigs of the new variety are 6" to 8" in length and 3/16" to ⅛" in diameter with internode spacing of ¾. The twigs surface is smooth and is Greyed-Red Group 178C. The branches are 28" to 40" in length and ⅜" to ¼" in diameter with internode spacing of 1¼". The branch surface is smooth and is Yellow-Green Group 146B.

The typical observed trunk diameter of the new variety on a 6-foot tall specimen is 1", measured at ½" above crown of the instant tree. The texture is smooth and is Greyed-Green Group 198C. The height and spread of a 15-year-old tree should be 25' in height and 10' wide in spread.

The blossom appearance of the new variety is similar to that of the genus. The new variety forms inconspicuous blooms which are perfect, apetalous. Crimson maroon flowers, Red-Purple Group 59C with ⅓" crimson stamens Red-Purple Group 61B with yellow anthers Yellow Group 13A. Buds generally opening to Red-Purple Group 57 B. The new variety bud shape is vegetative-stalked, tomentulous, with two outer scales, with typical length of ⅛" and diameter of ⅛", similar to the species, *Parrotia persica.*

The overall configuration of the flowers is generally typical of the genus. The flowers are perfect, apetalous and sparse. Blossoming commonly occurs during late March at Salem, Oreg., U.S.A., where it commonly extends over approximately 1-2 weeks depending upon the weather conditions that are encountered. The flowers are commonly borne attached to stem. Each stem has multiple flowers which are not fragrant. The reproductive organs are typical of a *Parrotia persica* and other species and cultivars of angiosperm flowering plants.

During observations to date, fruit has not been formed and is not considered to be ornamental in nature.

When grown at Salem, Oreg., U.S.A., the new variety has exhibited disease resistance under observations to date and has not been affected to any degree by common *Parrotia* diseases or by insects which commonly attack *Parrotia*. The new variety has proven to be hardy when tested in U.S.D.A. Hardiness Zone 5.

The nearest cultivar to the new variety is the un-patented 'Vanessa'. The new variety has a leaf size that is approximately 20-25% smaller in length and width than 'Vanessa'. The branching structure of the new variety has a more densely branched and narrow habit. The emerging leaves on the new variety are dark purple, the emerging leaves on 'Vanessa' are green. The new variety has a multi-phased fall color of red, burgundy, orange and yellow, 'Vanessa' fall color is bright yellow.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claim which follows.

What is claimed is:

1. A new and distinct cultivar of Ornamental *Parrotia persica* plant named 'JL Columnar' as described and illustrated herein.

* * * * *